(12) United States Patent
Feng

(10) Patent No.: US 8,068,228 B2
(45) Date of Patent: Nov. 29, 2011

(54) IN-PLANE OPTICAL METROLOGY

(75) Inventor: Ye Feng, Portland, OR (US)

(73) Assignee: Nanometrics Incorporated, Milpitas, CA (US)

( * ) Notice: Subject to any disclaimer, the term of this patent is extended or adjusted under 35 U.S.C. 154(b) by 222 days.

(21) Appl. No.: 11/835,206

(22) Filed: Aug. 7, 2007

(65) Prior Publication Data

US 2009/0040613 A1    Feb. 12, 2009

(51) Int. Cl.
     *G01N 21/55*        (2006.01)
(52) U.S. Cl. .......................................... 356/445; 385/37
(58) Field of Classification Search .......... 356/601–623, 356/445–448, 237.1–237.5; 385/12, 129, 385/37
See application file for complete search history.

(56) References Cited

U.S. PATENT DOCUMENTS

| | | | |
|---|---|---|---|
| 6,043,876 A * | 3/2000 | Holliday et al. | 356/237.1 |
| 6,239,876 B1 * | 5/2001 | Brandenberg | 356/481 |
| 6,580,501 B2 * | 6/2003 | Cannon | 356/237.1 |
| 6,809,810 B2 * | 10/2004 | Carrillo | 356/246 |
| 6,944,369 B2 * | 9/2005 | Deliwala | 385/30 |
| 7,065,272 B2 | 6/2006 | Taillaert et al. | |
| 2003/0011775 A1 | 1/2003 | Soljacic et al. | |
| 2007/0081169 A1 | 4/2007 | Diebold et al. | |

FOREIGN PATENT DOCUMENTS

WO     2006/048660 A1     5/2006

OTHER PUBLICATIONS

Taillaert, Dirk, et al., "A Compact Two-Dimensional Grating Coupler Used as a Polarization Splitter", IEEE Photonics Technology Letters, vol. 15, No. 9, Sep. 2003, 1249-1251.
Taillaert, Dirk, et al., "An Out-of-Plane Grating Coupler for Efficient Butt-Coupling Between Compact Planar Waveguides and Single-Mode Fibers", IEEE Journal of Quantum Electronics, vol. 38, No. 7, Jul. 2002, 949-955.
Bogaerts, Wim, et al., "A polarization-diversity wavelength duplexer circuit in silicon-on-insulator photonic wires", Optics Express 1567, vol. 15, No. 4, Feb. 19, 2007, 12 pages.
Mekis, Attila, et al., "High Transmission through Sharp Bends in Photonic Crystal Waveguides", Physical Review Letters, vol. 77, No. 18, Oct. 28, 1996, 3787-3790.
Taillaert, Dirk, et al., "Compact efficient broadband grating coupler for silicon-on-insulator waveguides", Optics Letters, vol. 29, No. 23, Dec. 1, 2004, 2749-2751.

* cited by examiner

*Primary Examiner* — Hoa Pham
(74) *Attorney, Agent, or Firm* — Silicon Valley Patent Group LLP

(57) ABSTRACT

A structure that is located adjacent to a measurement target on a substrate is used to convert incident radiation from an optical metrology device to be in-plane with the measurement target. The structure may be, e.g., a grating or photonic crystal, and may include a waveguide between the structure and the measurement target. The in-plane light interacts with the measurement target and is reflected back to the structure, which converts the in-plane light to out-of-plane light that is received by the optical metrology device. The optical metrology device then uses the information from the received light to determine one or more desired parameters of the measurement target. Additional structures may be used to receive light that is transmitted through or scattered by the measurement target if desired.

8 Claims, 9 Drawing Sheets

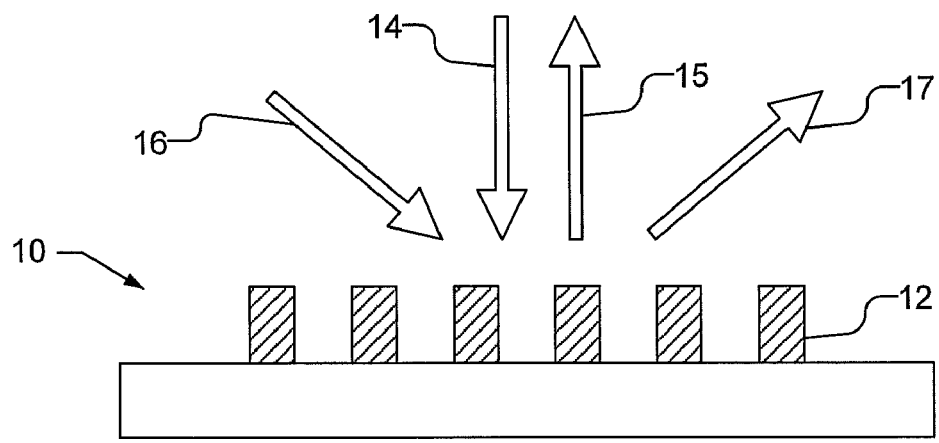
Fig. 1
(Conventional)

IN-PLANE OPTICAL METROLOGY

FIELD OF THE INVENTION

The present invention is related to optical metrology and, in particular, to metrology in which probe beam is controlled to be in-plane with the measurement target.

BACKGROUND

Optical metrology is commonly employed in process control applications in the semiconductor manufacturing industry due to optical metrology's non-contact and non-destructive nature. Two commonly used optical metrology techniques are reflectometry and ellipsometry.

In optical metrology, a sample is illuminated with broadband or single wavelength light and the light is detected and analyzed after it interacts with the sample. FIG. 1 illustrates a side view of a sample 10 with a grating 12 that is being illuminated with a probe beam 14 having a normal angle of incidence and a probe beam 16 having an oblique angle of incidence. Typically, but not always, the oblique angle of incidence probe beam 16 is used with an ellipsometer and the normal incidence probe beam 14 is used with a reflectometer. The probe beams 14 and 16 are illustrated as reflected from the grating 12 (which in the case of a diffraction grating is the zeroth order diffracted light) as beams 15 and 17, respectively. The normal incidence probe beam 14 and the reflected beam 15 are illustrated as laterally displaced, but it should be understood that these beams coincide due to their normal orientation.

As semiconductor geometries continue to shrink, increasing demands are placed on the optical metrology techniques. Moreover, the use of non-planar structures, such as FinFET devices, Intel's tri-gate and AMD's multigate device, provides additional challenges to optical metrology, as three-dimensional structural information is difficult to extract.

Accordingly, improved optical metrology devices and methods are desired.

SUMMARY

In accordance with one embodiment, an optical coupler is located adjacent to a measurement target on a substrate. The optical coupler converts incident radiation from an optical metrology device to be in-plane with the measurement target. The optical coupler may be, e.g., a grating or photonic crystal, and may include a waveguide between the optical coupler and the measurement target. The in-plane light interacts with and is reflected back to the optical coupler, which converts the in-plane light to out-of-plane light that is received by the optical metrology device. The optical metrology device then uses the information from the received light to determine one or more desired parameters of the measurement target. Alternatively, an additional optical coupler may be used to receive light that is transmitted through the measurement target if desired.

BRIEF DESCRIPTION OF THE DRAWINGS

FIG. 1 illustrates conventional optical metrology in which light has either an oblique angle of incidence or normal angle of incidence with respect to the target.

DETAILED DESCRIPTION

In accordance with an embodiment of the present invention, a target on a sample is probed using optical metrology with an in-plane radiation, i.e., the radiation incident on the target is parallel to the surface of the sample, which is said to have a 90° angle of incidence.

Figure 2A:
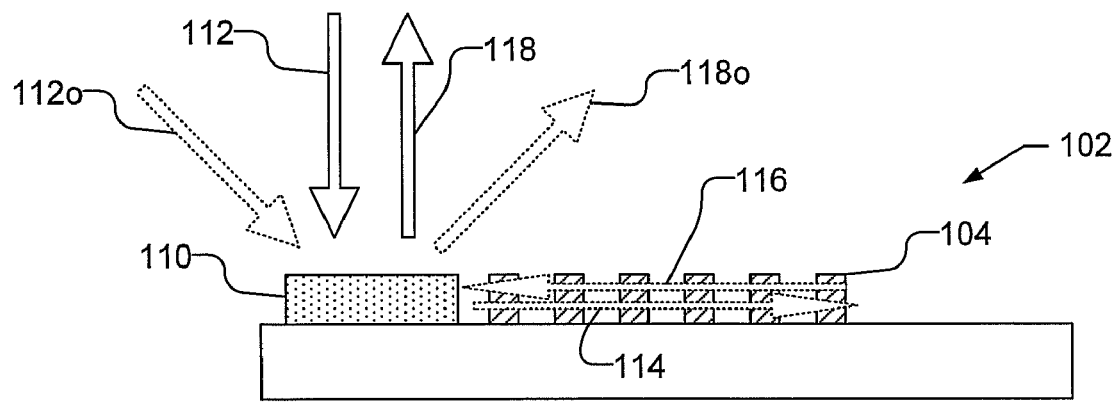
FIG. 2A illustrates a side view of in-plane metrology of a target using an optical coupler operating in a reflectance mode.

FIG. 2A illustrates a side view of target 104 on a sample 102, which may be, e.g., a semiconductor wafer, along with an optical coupler 110, which may be, e.g., a photonic crystal or a grating that produces the in-plane probe beam. A normal angle of incidence probe beam 112 is incident on the optical coupler 110 which is converted to the in-plane probe beam 114. The in-plane metrology of the target 104 in FIG. 2A is illustrated as being in reflectance mode, as the in-plane returning beam 116 is converted by the optical coupler 110 to the normal beam 118, which is received by the metrology device and analyzed appropriately.

In another embodiment, an oblique angle of incidence probe beam 112o (illustrated with dotted lines) may be used. The returning beam 116 is converted by the optical coupler 110 to another oblique angle beam 118o (illustrated with dotted lines), which may have the same (or different) magnitude and opposite direction. By way of example, the probe beam 112o may have an incidence angle of 65° and the oblique return beam 118o may have an incidence angle of −65° (although any angle may be used if desired).

Figure 2B:
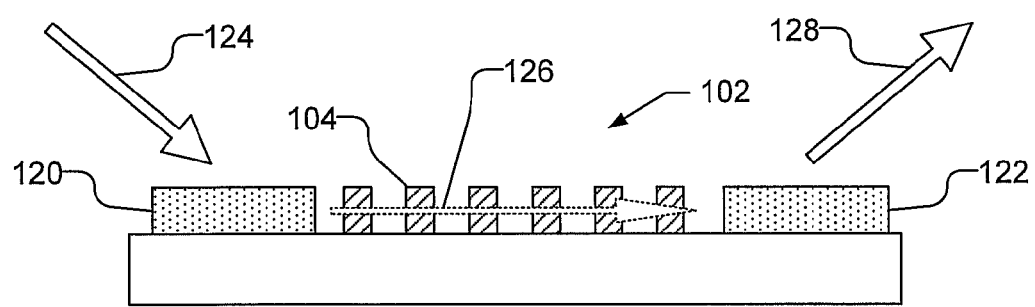
FIG. 2B illustrates a side view of in-plane metrology of a target using optical couplers operating in a transmittance mode.

While FIG. 2A illustrated in-plane optical metrology in reflectance mode, other modes, such as transmittance and scatter mode may be used. For example, FIG. 2B illustrates a side view of in-plane metrology of target 104 using optical couplers 120 and 122 operating in a transmittance mode. An oblique angle of incidence probe beam 124 is incident on the optical coupler 120, which converts the probe beam 124 to an in-plane probe beam 126. A second optical coupler 122 converts the in-plane probe beam 126 to an oblique returning beam 128, which is received by the metrology device and analyzed appropriately. It should be understood that if desired, the probe beam 124 and returning beam 128 need not be oblique, but may be normal, similar to that illustrated in FIG. 2A. For example, when the lateral dimensions of the structures in FIG. 2B are smaller than the beam size, the probe beam 124 and returning beam 128 can share the same beam path.

Figure 2C:
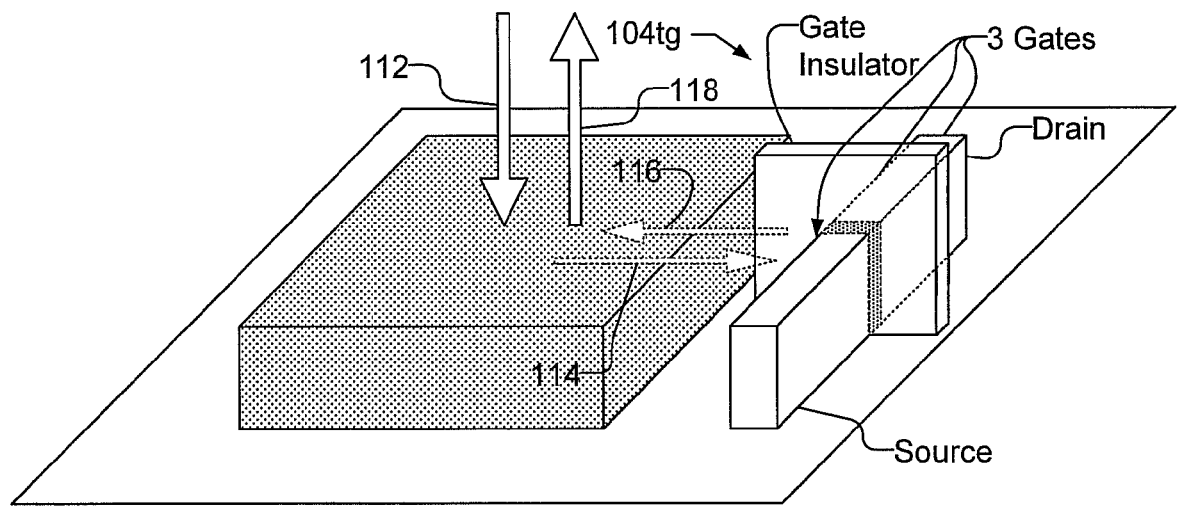
FIG. 2C illustrates a perspective view of in-plane metrology of a tri-gate target using an optical coupler operating in a reflectance mode.

FIG. 2C illustrates a perspective view of a tri-gate target 104tg on a sample 102, which may be, e.g., a semiconductor wafer, along with an optical coupler 110 operating in reflectance mode similar to FIG. 2A.

As illustrated in FIGS. 2A, 2B, and 2C, the optical coupler(s) is produced on the sample 102 along with the target to be measured. The optical metrology device, e.g., a reflectometer, ellipsometer, scatterometer, etc., directs the probe beam to be incident on the optical coupler as opposed to the target and receives the resulting beam from the optical coupler.

Figure 3:
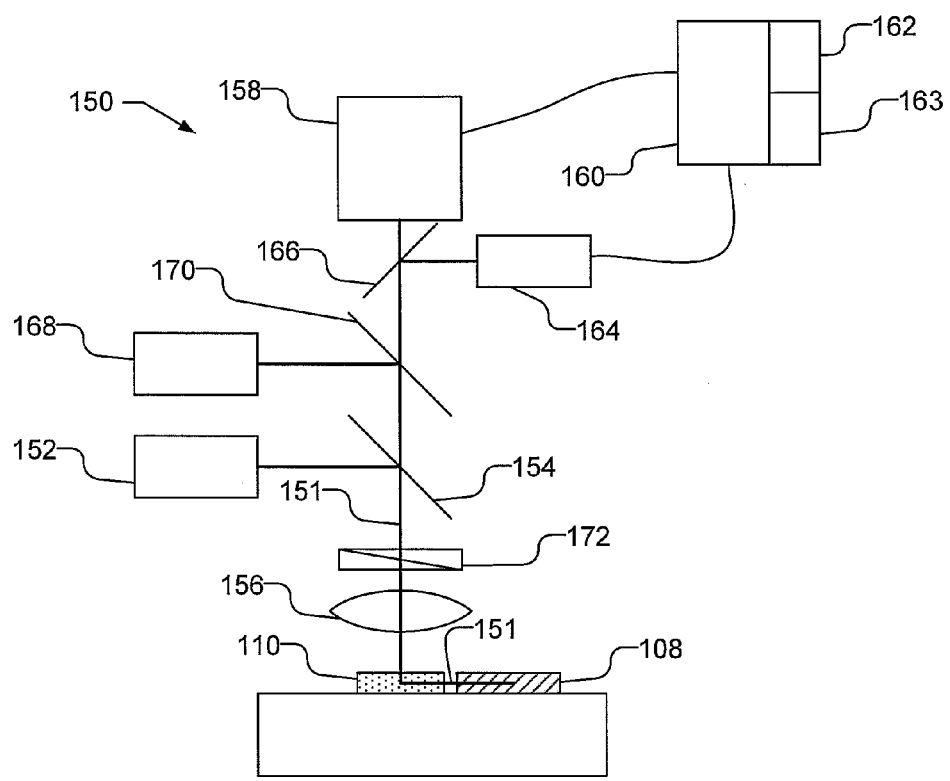
FIG. 3 illustrates a reflectometer performing in-plane metrology of a target and an optical coupler.

FIG. 3 illustrates one embodiment of a metrology device 150 that may be used with the optical coupler to perform in-plane metrology in accordance with an embodiment of the present invention. The metrology device illustrated in FIG. 3 is a normal incidence reflectometer 150, which includes a light source 152 that produces light that is directed along a beam path 151 towards the optical coupler 110. The light source 152 may be a single wavelength light source, such as a laser, or a broadband light source, such as a Xenon lamp or the like. By way of example, the light source 152 may produce one or more wavelengths in a range of 150 nm to 30 µm. Reflectometer 150 includes a beam splitter 154 that directs the light towards the sample 102. A lens 156 (or series of lenses) focus the light onto the optical coupler 110. As illustrated in FIG. 3, the optical coupler 110 directs the beam path 151 of the reflectometer 150 to be in-plane with the target 108 that is to be measured by the reflectometer 150.

The beam reflected by the target 108 is reflected in-plane along beam path 151 back to the optical coupler 110, which converts the reflected beam back to normal. The returning beam passes through the lens 156 and beam splitter 154 and is received by the detector 158. The detector 158 may detect the intensity of the returning beam and may be, e.g., a spectrometer if broadband light is used. In some embodiments, the polarization state of the returning beam may be detected, e.g., with the use of one or more polarizing elements, such as polarizing element 172. The detector 158 is coupled to a processor 160 that can control the operation of the metrology device, along with controlling the positioning of the metrology device with respect to the optical coupler. The processor 160 is a system that includes a computer and a computer-usable medium having computer-readable program code embodied therein for controlling the operation of the metrology device as well as analyzing the data obtained by the metrology system as described herein. The generation of computer-readable program code for controlling the operation of the metrology device and/or analyzing the data obtained by the metrology system is well within the abilities of those skilled in the art in light of the present disclosure. The processor 160 may include a reporting device 162 that reports the results of the measurement. The reporting device 162 may be, e.g., a display, printer, an alarm to indicate when the measurement is out of specification, or memory to store the result of the measurement.

The processor 160 uses the data obtained by the in-plane probe beam to determine the value of the desired parameter of the target 108. The optical response of sub-wavelength scattering can be calculated with known electromagnetic methods, for example, rigorous coupled wave analysis (RCWA) or finite-difference time-domain (FDTD) methods. An empirical or regression analysis may be used to correlate a return signal, such as intensity or polarization, to the change of target process parameters. The correlation may be pre-generated and stored in a library, e.g., in memory 163 in the processor 160 or in other appropriate medium. Alternatively, a correlation formed through regression analysis may be performed in real-time, e.g., by processor 160. The processor 160 may compare the data obtained by the in-plane probe beam to the correlations stored in the library or generated in real-time in order to determine the value of desired parameter.

The reflectometer 150 may include additional elements such as a camera 164 and a flip mirror 166 or pin-hole mirror 166 that are used to assist in positioning the reflectometer 150 with the optical coupler 110. Additionally, a white light source 168 and beam splitter 170 may be included, e.g., if the light source 152 is a laser. Additionally, one or more polarizing elements 172 may be used with reflectometer if desired.

Figure 4:
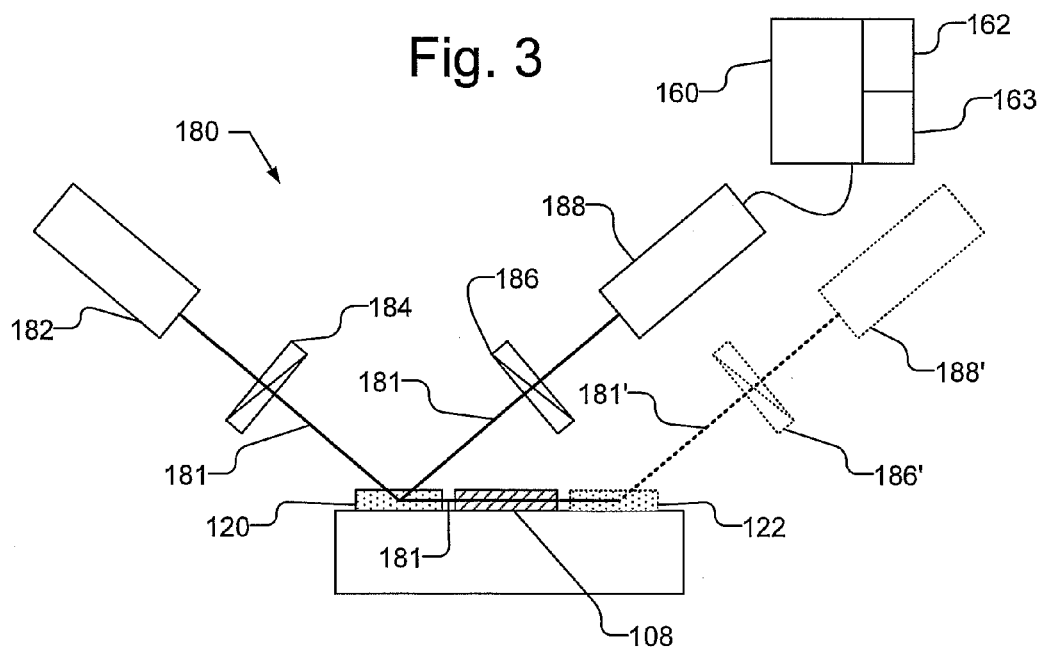
FIG. 4 illustrates an ellipsometer performing in-plane metrology of a target with optical couplers.

FIG. 4 illustrates another embodiment of a metrology device 180 that may be use the optical coupler to perform in-plane metrology in accordance with an embodiment of the present invention. FIG. 4 illustrates an ellipsometer 180 with an optical coupler 120 performing in-plane metrology on a measurement target 108 in reflectance mode. The ellipsometer 180 includes a light source 182, which may be a single wavelength or broadband light source, and a polarizer 184. The light source 182 produces light along the beam path 181, which is incident on optical coupler 120. Additional elements may be provided along beam path 181, such as lenses to focus the light on the optical coupler 120, particularly if broadband light is used.

As illustrated in FIG. 4, the optical coupler 120 directs the beam path 181 of the ellipsometer 180 to be in-plane with the target 108 that is to be measured by the ellipsometer 180. The light that is returned by the target 108 is directed by the optical coupler 120 along the beam path 181 to an analyzer 186 and to a detector 188. The detector 188 is coupled to a processor 160, such as that described above.

As illustrated by dotted lines in FIG. 4, the ellipsometer 180 may alternatively operate in transmittance mode and use a second optical coupler 122. As illustrated in FIG. 4, the second optical coupler 122 directs the light that is transmitted through the target 108 along the beam path 181' to an analyzer 186' and to a detector 188'.

Figure 5:
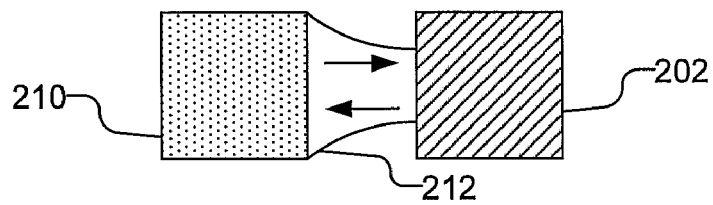
FIG. 5 illustrates a plan view of an optical coupler and a target with the optical coupler operating in reflectance mode through a waveguide.

FIGS. 5-9 illustrate various configurations that are possible with one or more optical couplers and one or more targets on a sample. The various configurations depend on factors such as the type of target to be measured and the type of metrology device being used. The in-plane probe beam may be confined in two dimensions, e.g., using a waveguide, or confined in one dimension, e.g., without a waveguide. By way of example, FIG. 5 illustrates a plan view of an optical coupler 210 and a target 202 with the optical coupler 210 operating in reflectance mode through a waveguide 212, as illustrated by the arrows. The use of a waveguide 212 may be particularly advantageous, e.g., when the optical coupler 210 cannot be located in close proximity to the target 202, when a diffraction-limited point source is needed for target illumination, or when the minimization of optical losses is necessary.

Figure 6:
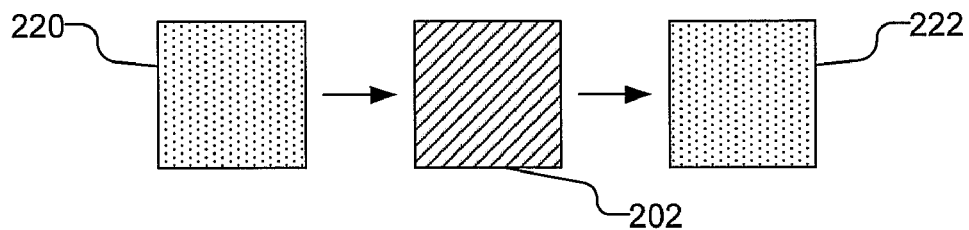
FIG. 6 illustrates a plan view of optical couplers and a target with the optical couplers operating in transmittance mode without a waveguide.
Figure 7:
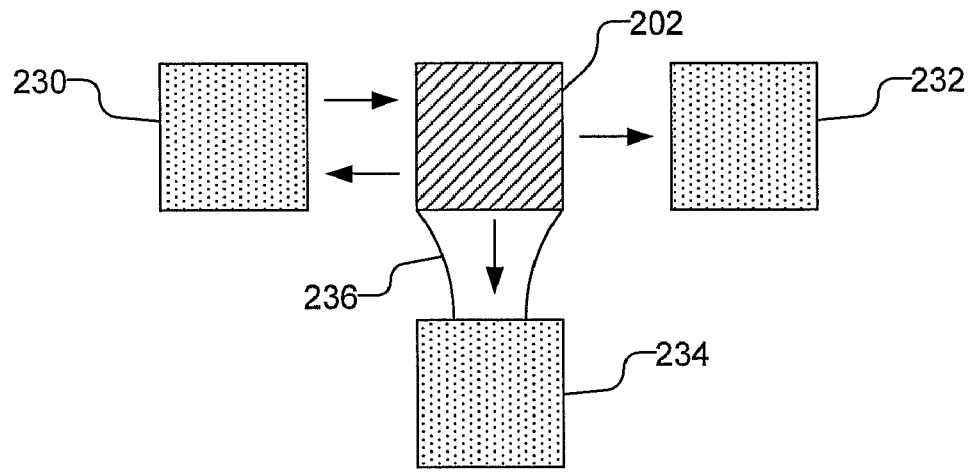
FIG. 7 illustrates a plan view of optical couplers and a target with the optical couplers operating in reflectance, transmittance, and scattering mode with and without waveguides.

FIG. 6 illustrates a plan view of optical couplers 220 and 222 and a target 202 with the optical couplers 220, 222 operating in transmittance mode without a waveguide, as illustrated by the arrows. FIG. 7 illustrates a plan view of optical couplers 230, 232, and 234 and a target 202 with the optical couplers operating in reflectance, transmittance, and a scattering mode, respectively, as illustrated by the arrows. Moreover, a waveguide 236 is used with the optical coupler 234, which receives light that is scattered from the target 202.

Figure 8:
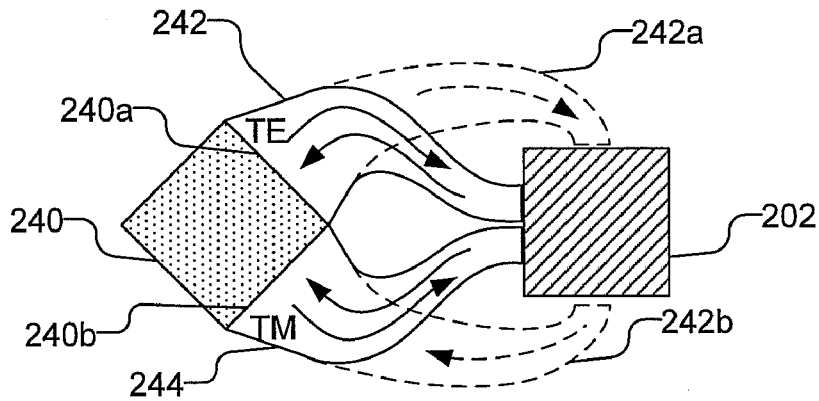
FIG. 8 illustrates a plan view of an optical coupler and a target with the optical coupler providing differently polarized light to the target through waveguides.

FIG. 8 illustrates a plan view of an optical coupler 240 and a target 202 with the optical coupler 240 coupled to the target 202 through two waveguides 242 and 244. A photonic crystal optical coupler 240 produces light having different polarization states, e.g., TE and TM, from adjacent edges 240a and 240b of the optical coupler 240. Waveguide 242 is used to guide TE polarized light from edge 240a to the target 202 while waveguide 244 is used to guide TM polarized light from edge 240b to the target 202. The optical coupler 240 is illustrated as operating in reflecting mode, with the reflecting light returning via waveguides 242 and 244 to the optical coupler 240, which can then be detected by the metrology device. The changes to the TE and TM light caused by the target 202 can then be analyzed by the metrology device. Thus, in one embodiment, the optical coupler 240 and target 202 are operating in an interferometer configuration. If desired, the waveguides 242 and 244 may guide the light from the optical coupler 240 to be incident on the target 202 at orthogonal orientations, e.g., as illustrated by broken lines 242a. Moreover, the optical coupler 240 may operate in transmission mode with the use of waveguides 242a and 242b illustrated in broken lines.

Figure 9:
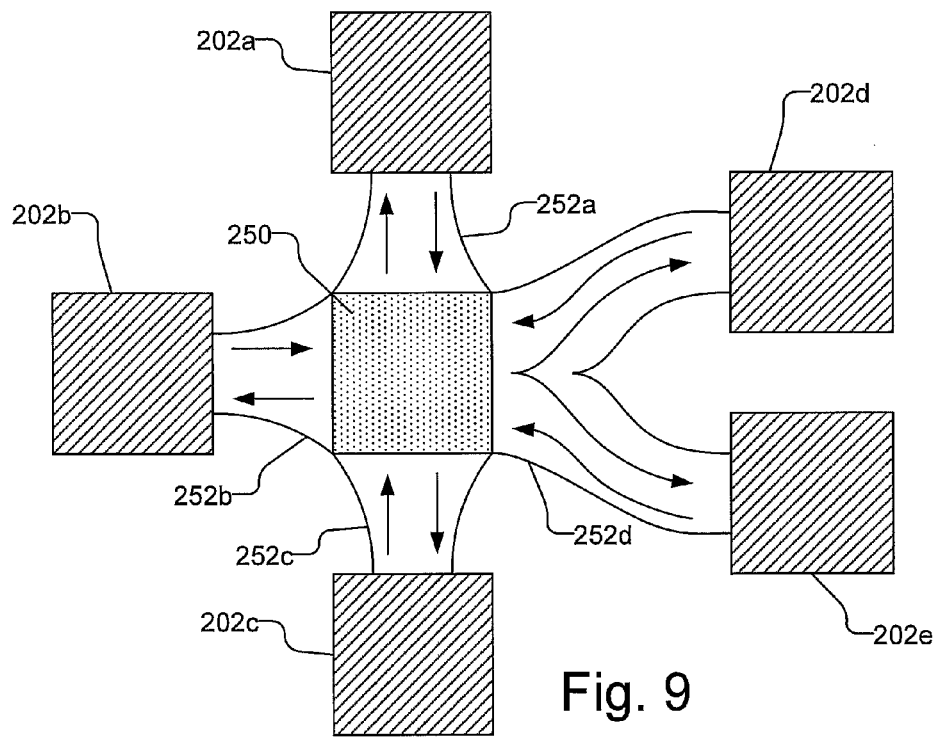
FIG. 9 illustrates a plan view of an optical coupler with a plurality of targets with the optical coupler operating in reflectance mode through waveguides.

FIG. 9 illustrates a plan view of an optical coupler 250 with a plurality of targets 202a, 202b, 202c, 202d, and 202e (sometimes collectively referred to as 202), with the optical coupler 250 coupled to each target 202 through waveguides 252a, 252b, 252c, and 252d (sometimes collectively referred to as 252). As illustrated in FIG. 9, the waveguide 252d is split to provide light to two separate targets 202d and 202e. The targets 202 may be the same or different types of targets. The optical coupler 250 is illustrated as operating in reflecting mode, with the reflecting light returning via waveguides 252 to the optical coupler 250, which can then be detected by the metrology device.

Figure 10:
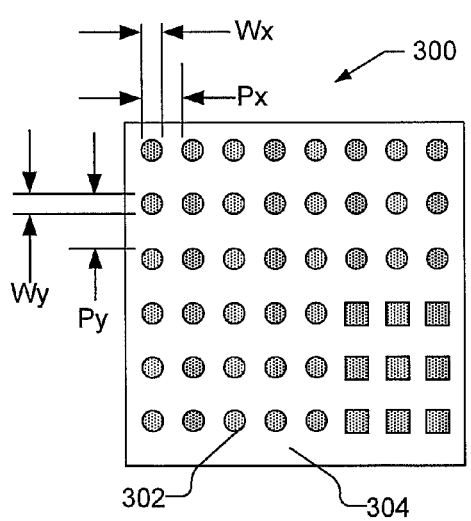
FIG. 10 illustrates a plan view of an optical coupler that is a photonic crystal.

FIG. 10 illustrates a plan view of an optical coupler 300 that is a photonic crystal. The photonic crystal optical coupler 300 includes an array of elements 302 which have a different index of refraction than the surrounding material 304. For example, the elements 302 may be a different material than the surrounding material 304 or may simply be air. The elements 302 may have different shapes, including circular, rectangular, oval or any other desired shape. The width Wx and pitch Px along one axis may differ from the width Wy and pitch Py along the other axis. The specific configuration and materials of the photonic crystal optical coupler 300 to produce in-plane light is dependent on the design of the angle of incidence and wavelength or wavelengths of light used by the metrology device, as well as process technology, such as the use of Si or III-V and the minimum printable feature size.

Figure 11:
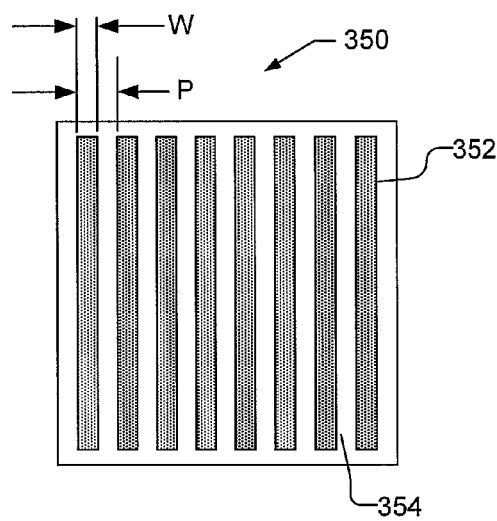
FIG. 11 illustrates a plan view of an optical coupler that is a grating.

FIG. 11 illustrates a plan view of another embodiment of an optical coupler 350 that is a grating. The grating optical coupler 350 includes a series of lines 352 and spaces 354 that are manufactured from materials having different indices of refraction. The lines 352 have a width W and pitch P that are configured to produce the desired in-plane light, which is a high order diffracted light, e.g., $1^{st}$ order or $2^{nd}$ order. As with the photonic crystal optical coupler 300, described above, the specific configuration and materials of the grating optical coupler 350 to produce in-plane light is dependent on the design of the angle of incidence and wavelength or wavelengths of light used by the metrology device, as well as process technology, such as the use of Si or III-V and the minimum printable feature size.

Producing an optical coupler and waveguide is discussed, e.g., in U.S. Pat. No., 7,065,272, and in "An Out-of-Plane Grating Coupler for Efficient Butt-Coupling Between Compact Planar Waveguides and Single-Mode Fibers", D. Taillaert, et al., IEEE Journal of Quantum Electronics, vol. 38, No. 7, (July 2002), and "A compact two-dimensional grating coupler used as a polarization splitter," D. Taillaert et al., IEEE Photonics Technol. Lett. 15, 1249-1251 (2003), all of which are incorporated herein by reference in their entirety.

Figure 12:
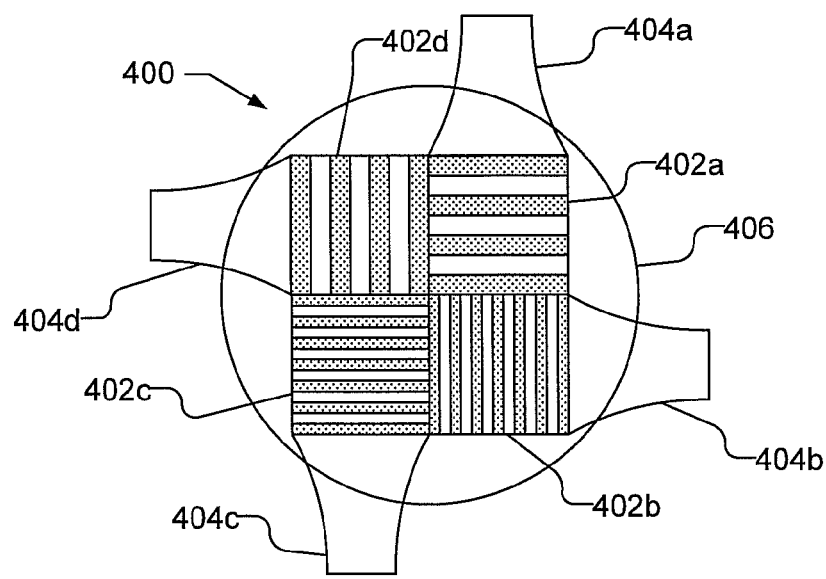
FIG. 12 illustrate a plan view of an optical coupler that includes a plurality of different gratings with waveguides and illustrates the spot size of the incident light is larger than the size of the optical coupler.

FIG. 12 illustrate a plan view of another embodiment of an optical coupler 400 that includes a plurality of gratings 402a, 402b, 402c, and 402d (sometimes collectively referred to as gratings 402), with separate waveguides 404a, 404b, 404c, and 404d (sometimes collectively referred to as gratings 404). FIG. 12 also illustrates the illumination spot 406 of the incident light from the metrology device. As can be seen, the spot size of the illumination may be larger than the optical coupler 400. Each grating 402 in the optical coupler 400 may be configured to produce in-plane light with a different wavelength or range of wavelengths. The waveguides 404 may then be used to guide the light from each grating to the same target or different targets.

Figure 13:
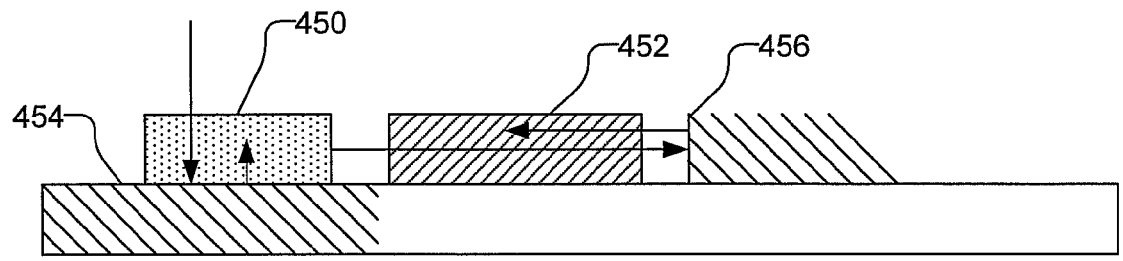
FIG. 13 illustrates a side view of an optical coupler and target with vertical and lateral confinement.

FIG. 13 illustrates a side view of an optical coupler 450 with a target 452 in which there are vertical and lateral confinement areas 454 and 456, respectively. The vertical confinement area 454 reflects light that is transmitted through the optical coupler 450 from the metrology device back into the optical coupler, as illustrated by arrows, and then diffracted towards the target. Additionally, the vertical confinement ensures that light returning to the optical coupler 450 from the target 452 is transmitted in the correct direction, i.e., towards the metrology device, by reflecting any downward coupled light.

Similarly, the lateral confinement area 456 reflects light that is transmitted through the target 452 back through the target 452 towards the optical coupler 450. Thus, the lateral confinement area 456 allows the optical coupler 450 to operate in both reflection mode, i.e., light reflected directly from the target 452 back to the optical coupler 450, as well as in transmission mode, i.e., light transmitted through target 452 is reflected back through the target 452 to the optical coupler 450.

Figure 14:
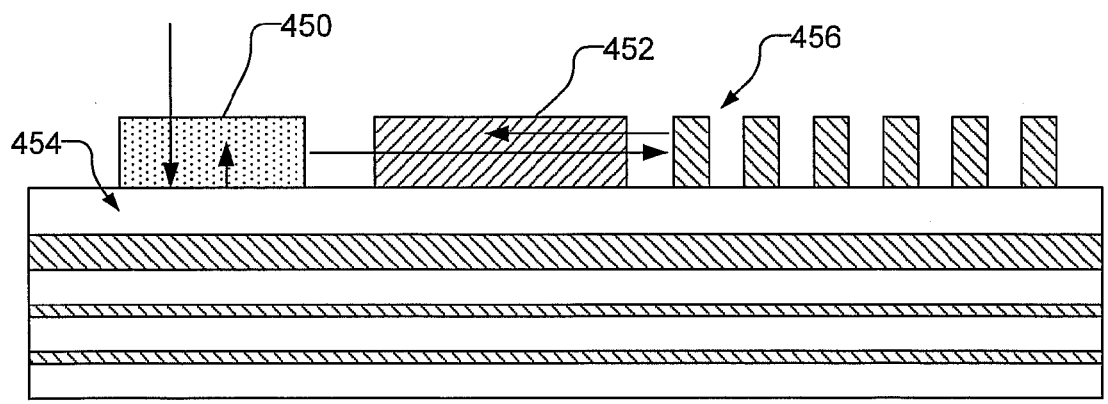
FIG. 14 illustrates another side view of an optical coupler and target with vertical and lateral confinement.

The vertical and lateral confinement areas 454 and 456 may be produced by materials of high reflectance, such as metals, or alternatively with the use of distributed Bragg reflectors, as schematically illustrated in FIG. 14. Moreover, the vertical confinement area 454 may extend under the target 452 if desired, as illustrated in FIG. 14.

Figure 15:
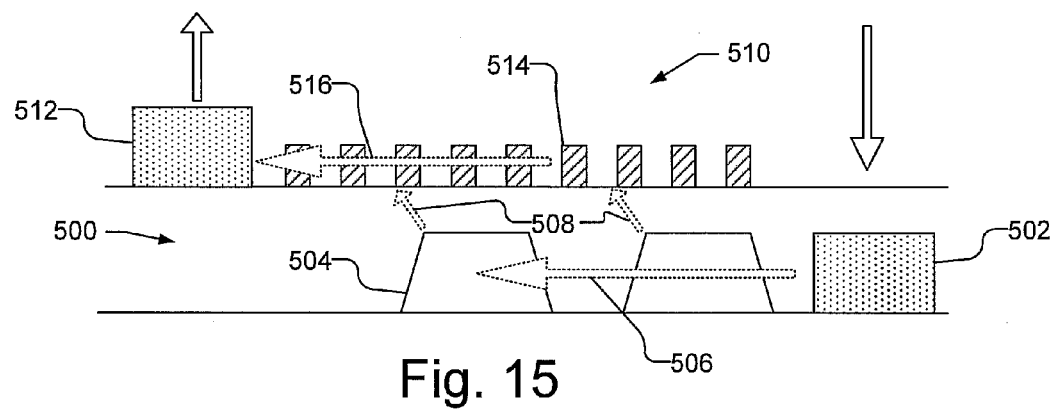
FIG. 15 illustrates a side view of in-plane metrology in which overlying layers are optically coupled.

In another embodiment, the in-plane metrology using an optical coupler may be performed with optically coupled overlying layers. FIG. 15 illustrates a side view of optically coupled overlying layers 500 and 510. The bottom layer 500 includes an optical coupler 502 and a first target 504 that is composed of a first periodic structure, which may be, e.g., shallow trench isolation (STI) structures. The top layer 510 includes another target 514 of periodic structures and a second optical coupler 512.

As illustrated in FIG. 15, light is incident on the optical coupler 502 that converts the light to in-plane light, illustrated by arrow 506, that is incident on the first target 504. The first target 504 is optically coupled to the second target 514, e.g., through diffraction illustrated by arrows 508. Accordingly, the second optical coupler 512 receives the light from the second target 514, as illustrated by arrow 516 and couples the light out of plane to be received by the metrology device.

Figure 16:
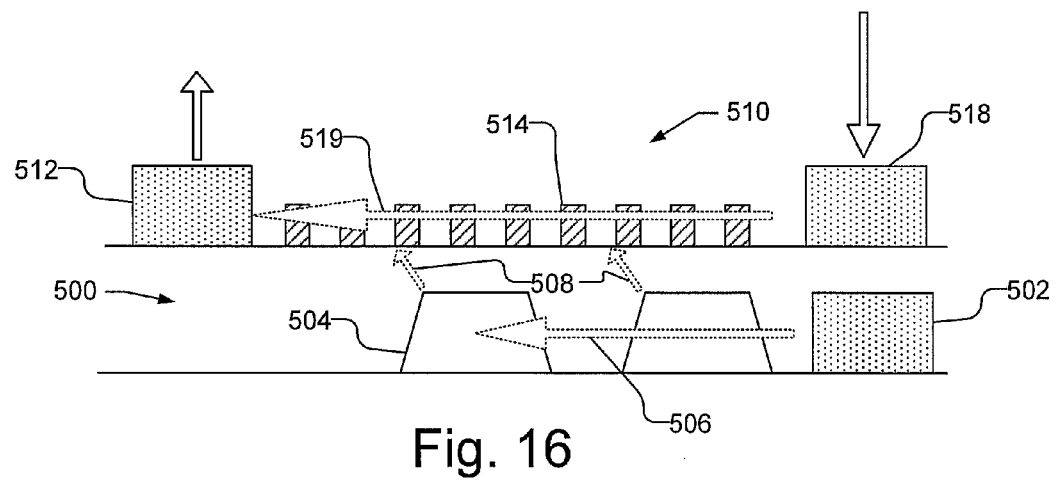
FIG. 16 illustrates another side view of in-plane metrology in which overlying layers are optically coupled in an interferometry application.

If desired, additional optical couplers may be used, e.g., as illustrated in FIG. 16. As illustrated in FIG. 16, an optical coupler 518 on the top layer 510 receives the incident light and couples the light in-plane to the second target 514. Light that is transmitted through the optical coupler 518 is received by optical coupler 502 on the bottom layer 500. The optical coupler 512, thus, receives light from the second target 514 from the top optical coupler 518 (illustrated by arrow 519) and light from the first target 504 via the bottom optical coupler 502 (illustrated by arrows 506 and 508), in an interferometry application.

Figure 17A:
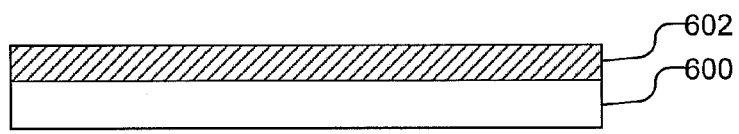
FIGS. 17A-17C illustrate cross-sectional views of producing an optical coupler and target using the same processing steps.
Figure 17B:
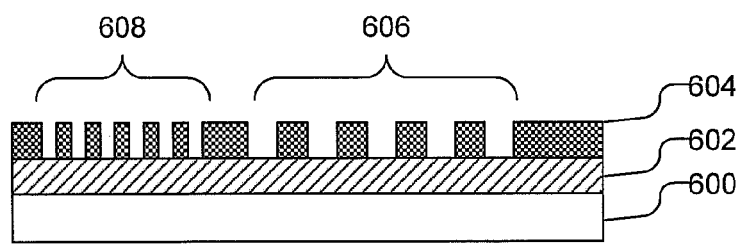

FIGS. 17A-17E illustrate cross-sectional views of one embodiment of producing an optical coupler and target in which the same processing steps are used. FIG. 17A illustrates a substrate 600 with an overlying layer 602. The substrate 600 may be, e.g., silicon, while layer 602 may be any desired material in which a target is to be formed. It should be understood that there may be many layers between the substrate 600 and the overlying layer 602, but for the sake of simplicity, intervening layers are not illustrated.

A layer of photoresist 604 is spun on or otherwise deposited over layer 602. The photoresist layer 604 is exposed, developed and selectively removed in a conventional manner to form a target area 606 and an optical coupler area 608, resulting in the structure illustrated in FIG. 17B. As illustrated, the target area 606 is a grating and the optical coupler area 608 is a grating or photonic crystal. It should be understood that the target area 606 may be any desired target and need not be a grating.

Figure 17C:
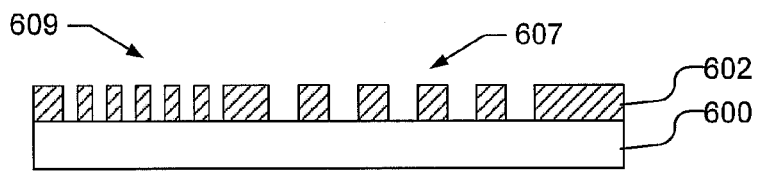

The layer 602 is then etched to form the optical coupler 609 and the target 607 and the photoresist layer 604 is stripped, resulting in the structure illustrated in FIG. 17C. As can be seen, the optical coupler 609 is formed in the same layer and of the same material as the target 607.

Figure 17D:
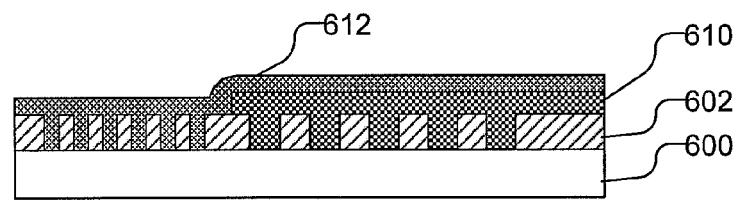
FIGS. 17D-17E illustrate cross-sectional views of producing an optical coupler and target with a dielectric contrast.
Figure 17E:
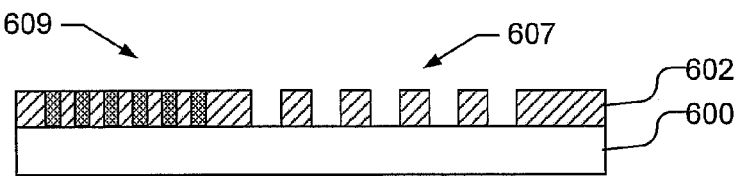

If desired, an additional layer may be deposited over the layer 602 and polished back, e.g., through chemical mechanical polishing, to form the optical coupler 609, the target 607 or both. For example, in one embodiment, the target 607 may be protected by a photoresist 610, while an additionally layer 612 is deposited as illustrated in FIG. 17D. After polishing and stripping the photoresist 610, the optical coupler 609 will include two materials, e.g., of different optical properties, n and k, while the target 607 does not include the second material, as illustrated in FIG. 17E.

It should be understood that other process steps may be used to generate an optical coupler along with the target. For example, in another embodiment, the optical coupler and the target are not produced with the same materials. FIGS. 18A-18D, by way of example, illustrate cross-sectional views of an embodiment of producing an optical coupler and target on the same layer, but out of different materials.

Figure 18A:
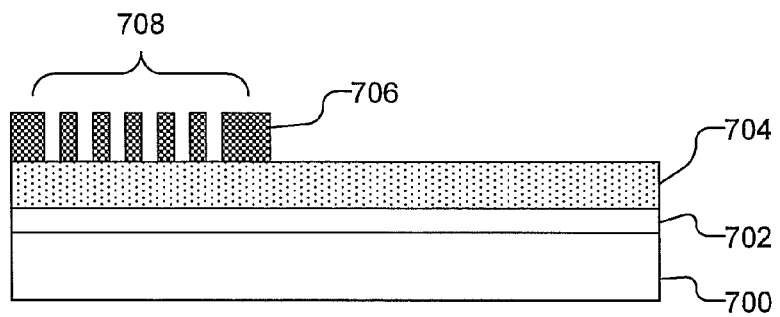
FIGS. 18A-18D illustrate cross-sectional views of producing an optical coupler and target using different processing steps.

FIG. 18A illustrates a substrate 700 with a layer 704 of material in which the optical coupler will be formed and an underlying layer 702. It should be understood that additional (or no) underlying layers may be present. The substrate 700 may be, e.g., silicon, while layer 704 may be any desired material. A layer of photoresist 706 is deposited, exposed and selectively removed to form the optical coupler area 708, as illustrated in FIG. 18A.

Figure 18B:
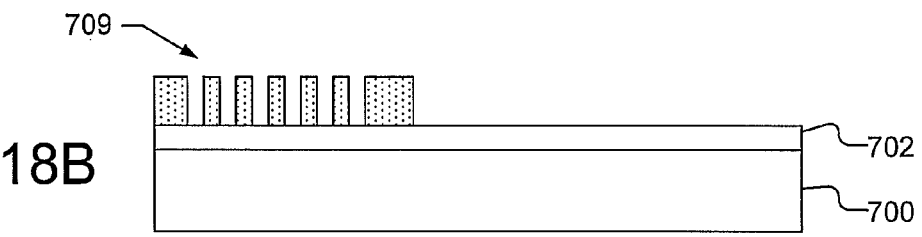
Figure 18C:
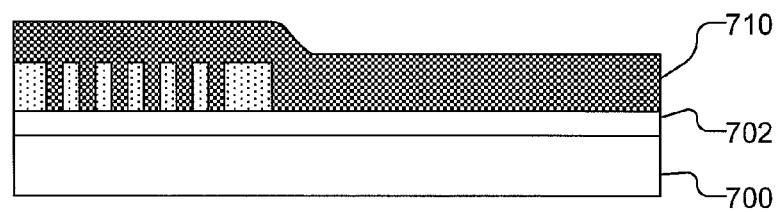
Figure 18D:
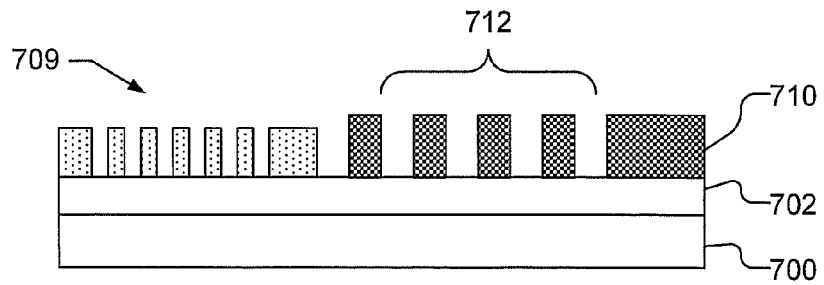

The exposed material in layer 704 is removed and the remaining photoresist is removed to form the optical coupler 709, as illustrated in FIG. 18B. Another layer of photoresist 710 is then deposited forming the structure illustrated in FIG. 18C. The photoresist 710 is then exposed, developed and selectively removed to form the target area 712 illustrated in FIG. 18D. The optical coupler 709 can be used for the in-plane optical measurement of target area 712 in the photoresist 710.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
   generating a beam of radiation;
   focusing the beam of radiation to form an incident beam of radiation on an optical coupler formed at a location that is laterally adjacent to a structure to be measured, the structure and the optical coupler formed on a substrate;
   converting the incident beam of radiation with the optical coupler to be parallel with the substrate and incident on and interacting with the structure to produce return radiation;
   converting the return radiation to be non-parallel with the substrate;
   detecting the return radiation;
   determining a measurement parameter of the structure using the detected return radiation; and
   reporting the determined measurement parameter, wherein reporting the determined measurement parameter comprises displaying the determined measurement parameter or storing the measurement parameter.

2. The method of claim 1, wherein the return radiation is converted to be non-parallel with the substrate at the same location that the incident beam of radiation is converted to be parallel with the substrate.

3. The method of claim 1, wherein the return radiation is converted to be non-parallel with the substrate at a different location than the location where the incident beam of radiation is converted to be parallel with the substrate.

4. The method of claim 1, wherein converting the incident beam of radiation and converting the return radiation is performed using a photonic crystal or a grating.

5. The method of claim 1, the method further comprising guiding radiation to the structure after converting the incident beam of radiation to be parallel with the substrate.

6. The method of claim 1, further comprising guiding the return radiation to a location where the return radiation is converted to be non-parallel with the substrate.

7. The method of claim 1, wherein the incident beam of radiation is normally incident on the substrate.

8. The method of claim 1, wherein the return radiation is converted to be normal to the substrate.

* * * * *